(12) United States Patent
Peters

(10) Patent No.: US 7,887,478 B2
(45) Date of Patent: Feb. 15, 2011

(54) PERCUTANEOUS GAS-LINE

(75) Inventor: William Suttle Peters, Auckland (NZ)

(73) Assignee: Sunshine Heart Company Pty Ltd, Birchgrove, New South Wales (AU)

( * ) Notice: Subject to any disclaimer, the term of this patent is extended or adjusted under 35 U.S.C. 154(b) by 417 days.

(21) Appl. No.: 10/595,603

(22) PCT Filed: Oct. 28, 2004

(86) PCT No.: PCT/AU2004/001485
§ 371 (c)(1),
(2), (4) Date: Apr. 28, 2006

(87) PCT Pub. No.: WO2005/042082
PCT Pub. Date: May 12, 2005

(65) Prior Publication Data
US 2007/0021830 A1    Jan. 25, 2007

(30) Foreign Application Priority Data
Oct. 31, 2003    (AU) ............................... 2003906067

(51) Int. Cl.
*A61M 1/10* (2006.01)
*A61M 5/00* (2006.01)
(52) U.S. Cl. ............................... 600/16; 600/17; 600/18
(58) Field of Classification Search .................. 600/16, 600/17, 18
See application file for complete search history.

(56) References Cited

U.S. PATENT DOCUMENTS

| 0,283,660 A | 8/1883 | Reed |
| 0,929,571 A | 7/1909 | Dubied |
| 1,576,397 A | 7/1925 | Yanagi |
| 1,719,316 A | 7/1929 | Appleton |
| 3,467,077 A | 9/1969 | Cohen |
| 3,552,383 A | 1/1971 | Krueger et al. |

(Continued)

FOREIGN PATENT DOCUMENTS

AU    2003277983    6/2008

(Continued)

OTHER PUBLICATIONS

Seymour Furman et al., "Cardiac Support by Periaortic Diastolic Augmentation", New York Journal of Medicine, Aug. 1, 1970, pp. 1964-1969.

(Continued)

*Primary Examiner*—Carl H Layno
*Assistant Examiner*—Gary A Porter, Jr.
(74) *Attorney, Agent, or Firm*—Faegre & Benson LLP

(57) ABSTRACT

A percutaneous gas-line (10) for a medical device (14). The gas-line including a first gas-line part (10*a*) and a second gas-line part (10*b*). The first gas-line part (10*a*) is adapted to be wholly implanted in a patient and has a first end (10*a*') adapted for sealing connection to the medical device (14) and a second end (10*a*") with a connection fitting (20). The second gas-line part (10*b*) is adapted to be part-implanted and part-external and has a first (external) end (10*b*') adapted for sealing connection to an external driver (12) and a second (implanted) end (10*b*") adapted for removable sealing connection with the connection fitting (20) on the second end (10*a*") of the first gas-line part (10*a*).

15 Claims, 2 Drawing Sheets

U.S. PATENT DOCUMENTS

| | | |
|---|---|---|
| 3,597,766 A | 8/1971 | Buck |
| 4,014,318 A | 3/1977 | Dockum et al. |
| 4,051,840 A | 10/1977 | Kantrowitz et al. |
| 4,176,411 A | 12/1979 | Runge |
| 4,195,623 A | 4/1980 | Zeff et al. |
| 4,236,482 A | 12/1980 | Gingerich et al. |
| 4,256,094 A | 3/1981 | Kapp |
| 4,277,706 A | 7/1981 | Isaacson |
| 4,304,225 A | 12/1981 | Freeman |
| 4,454,891 A | 6/1984 | Dreibelbis et al. |
| 4,457,673 A | 7/1984 | Conley et al. |
| 4,459,977 A | 7/1984 | Pizon et al. |
| 4,515,587 A | 5/1985 | Schiff |
| 4,583,523 A | 4/1986 | Kleinke et al. |
| 4,594,731 A | 6/1986 | Lewkowicz |
| 4,630,597 A | 12/1986 | Kantrowitz et al. |
| 4,676,482 A | 6/1987 | Reece et al. |
| 4,697,574 A | 10/1987 | Karcher et al. |
| 4,763,646 A | 8/1988 | Lekholm |
| 4,771,765 A | 9/1988 | Choy et al. |
| 4,809,676 A | 3/1989 | Freeman |
| 4,813,952 A | 3/1989 | Khalafalla |
| 4,822,357 A | 4/1989 | Forster et al. |
| 4,881,939 A | 11/1989 | Newman |
| 4,957,477 A | 9/1990 | Lundback |
| 4,979,936 A | 12/1990 | Stephenson et al. |
| 5,089,017 A | 2/1992 | Young et al. |
| 5,197,980 A | 3/1993 | Gorahkov et al. |
| 5,205,810 A | 4/1993 | Guiraudon et al. |
| 5,222,980 A | 6/1993 | Gealow |
| 5,267,940 A | 12/1993 | Moulder |
| 5,273,518 A | 12/1993 | Lee |
| 5,290,249 A * | 3/1994 | Foster et al. ............... 604/174 |
| 5,300,111 A | 4/1994 | Panton et al. |
| 5,337,752 A | 8/1994 | Reeves |
| 5,344,385 A | 9/1994 | Buck et al. |
| 5,360,445 A | 11/1994 | Goldowsky |
| 5,372,573 A | 12/1994 | Habib |
| 5,429,584 A | 7/1995 | Chiu |
| 5,447,523 A | 9/1995 | Schaldach |
| 5,453,076 A | 9/1995 | Kiyota et al. |
| 5,511,551 A | 4/1996 | Sano et al. |
| 5,554,177 A | 9/1996 | Kieval et al. |
| 5,569,156 A | 10/1996 | Mussivand |
| 5,593,414 A | 1/1997 | Shipp et al. |
| 5,607,378 A | 3/1997 | Winston |
| 5,647,380 A | 7/1997 | Campbell et al. |
| 5,722,930 A | 3/1998 | Larson, Jr. et al. |
| 5,792,195 A | 8/1998 | Carlson et al. |
| 5,814,012 A * | 9/1998 | Fleenor et al. ............... 604/26 |
| 5,820,542 A | 10/1998 | Dobak, III et al. |
| 5,827,171 A | 10/1998 | Dobak, III et al. |
| 5,843,170 A | 12/1998 | Ahn |
| 5,975,140 A | 11/1999 | Lin |
| 5,980,488 A | 11/1999 | Heilman et al. |
| 6,030,336 A | 2/2000 | Franchi |
| 6,045,496 A | 4/2000 | Pacella et al. |
| 6,066,085 A | 5/2000 | Heilman et al. |
| 6,132,363 A * | 10/2000 | Freed et al. ............... 600/16 |
| 6,132,636 A | 10/2000 | Singh et al. |
| 6,210,318 B1 | 4/2001 | Lederman |
| 6,226,843 B1 | 5/2001 | Crainich |
| 6,251,061 B1 | 6/2001 | Hastings et al. |
| 6,432,039 B1 | 8/2002 | Wardle |
| 6,471,633 B1 | 10/2002 | Freed |
| 6,553,263 B1 | 4/2003 | Meadows et al. |
| 6,572,534 B1 | 6/2003 | Milbocker et al. |
| 6,585,635 B1 | 7/2003 | Aldrich |
| 6,616,596 B1 | 9/2003 | Milbocker |
| 6,626,821 B1 | 9/2003 | Kung et al. |
| 6,643,548 B1 | 11/2003 | Mai et al. |
| 6,808,483 B1 | 10/2004 | Ortiz et al. |
| 6,808,484 B1 | 10/2004 | Peters et al. |
| 6,984,201 B2 | 1/2006 | Khaghani et al. |
| 7,169,109 B2 | 1/2007 | Jansen et al. |
| 7,360,558 B1 | 12/2007 | Peters et al. |
| 7,347,811 B2 | 3/2008 | Peters et al. |
| 7,357,771 B2 | 4/2008 | Peters et al. |
| 7,513,864 B2 | 4/2009 | Kantrowitz et al. |
| 7,740,575 B2 | 6/2010 | Peters et al. |
| 7,765,003 B2 | 8/2010 | Miller et al. |
| 2003/0105497 A1 | 6/2003 | Zhu et al. |
| 2004/0073080 A1 | 4/2004 | Peters et al. |
| 2004/0097783 A1 | 5/2004 | Peters et al. |
| 2004/0097784 A1 | 5/2004 | Peters et al. |
| 2004/0147803 A1 | 7/2004 | Hegde et al. |
| 2006/0052866 A1 | 3/2006 | Gilles et al. |
| 2007/0093684 A1 | 4/2007 | Peters et al. |
| 2007/0129796 A1 | 6/2007 | Miller |
| 2007/0135677 A1 | 6/2007 | Miller et al. |
| 2007/0167898 A1 | 7/2007 | Peters et al. |
| 2008/0027270 A1 | 1/2008 | Peters et al. |
| 2008/0139873 A1 | 6/2008 | Peters et al. |
| 2008/0167515 A1 | 7/2008 | Peters et al. |

FOREIGN PATENT DOCUMENTS

| | | |
|---|---|---|
| DE | 1541311 | 11/1966 |
| EP | 0080348 B2 | 5/1988 |
| EP | 0363203 | 4/1990 |
| EP | 0216042 | 3/1991 |
| EP | 0601804 | 6/1994 |
| EP | 0364799 B1 | 5/1995 |
| EP | 1129736 | 9/2001 |
| FR | 2458288 | 1/1981 |
| FR | 2645739 | 10/1990 |
| FR | 2767874 | 3/1999 |
| GB | 2422114 | 4/2008 |
| JP | 9-502376 | 3/1997 |
| JP | 9-503933 | 4/1997 |
| JP | 10-328297 | 12/1998 |
| JP | H11-285529 | 10/1999 |
| JP | 2000-510006 | 8/2000 |
| WO | WO 92/08500 | 5/1992 |
| WO | WO 93/08874 | 5/1993 |
| WO | WO 95/05122 | 2/1995 |
| WO | WO 95/28127 | 10/1995 |
| WO | WO 97/40755 | 11/1997 |
| WO | WO 98/05289 | 2/1998 |
| WO | WO 98/14239 | 4/1998 |
| WO | WO 98/51367 | 11/1998 |
| WO | WO 99/02213 A1 | 1/1999 |
| WO | WO 99/04833 | 2/1999 |
| WO | WO 99/45981 | 9/1999 |
| WO | WO 00/012168 | 3/2000 |
| WO | WO 00/076288 | 12/2000 |
| WO | WO 01/13974 | 3/2001 |
| WO | WO 01/83001 A1 | 11/2001 |
| WO | WO 02/024254 | 3/2002 |
| WO | WO 02/024255 | 3/2002 |
| WO | WO 02/076305 | 10/2002 |
| WO | WO 03/011365 | 2/2003 |
| WO | WO 03/028787 | 4/2003 |
| WO | WO 2004/045677 | 6/2004 |
| WO | WO 2005/041783 | 5/2005 |
| WO | WO 2005/042063 | 5/2005 |
| WO | WO 2005/044338 | 5/2005 |
| WO | WO 2005/110512 | 11/2005 |
| WO | WO 2008/053469 | 5/2008 |
| WO | WO 2008/071223 | 6/2008 |

OTHER PUBLICATIONS

J.L. Stewart, "Aortic Cuff a Cardiac Assistance Device", Polytechnic Institute of Brooklyn, 1968, pp. 9-108.

Hiroshi Odaguchi et al., "Experimental Study of Extraaortic Balloon Counterpulsation as a Bridge to Other Mechanical Assists" ASAIO Journal, pp. 190-194, vol. 42, No. 3, Lippincott Williams & Wilkins/ASAIO, Hagerstown, MD, May 1, 1996. cited by other.

"Use of Heart Valve Sounds as Input to Cardiac Assist Devices", Research Disclosures, Mar. 1995.

Luisada et al., On the Function of the Aortic Valve and the Mechanism of the First and Second Sounds, Japanese Heart Journal, vol. 18(1), Jan. 1977, pp. 81-91.

International Search Report issued in PCT/AU00/00654, mailed Aug. 18, 2000, 5 pages.

International Search Report issued in PCT/AU2002/000974, mailed Oct. 11, 2002, 5 pages.

International Preliminary Examination Report issued in PCT/AU2002/000974, completed Aug. 11, 2003, 8 pages.

International Search Report issued in PCT/AU2001/01187, mailed Nov. 5, 2001, 3 pages.

International Preliminary Examination Report issued in PCT/AU2001/01187, completed May 2, 2002, 4 pages.

International Search Report and Written Opinion issued in PCT/AU2007/001188, mailed Oct. 4, 2007, 12 pages.

International Preliminary Report on patentability, Chapter II, issued in PCT/AU2007/001188, completed Mar. 11, 2008, 8 pages.

International Search Report issued in PCT/AU2003/001450, mailed Feb. 2, 2004, 2 pages.

International Preliminary Examination Report issued in PCT/AU2003/001450, completed Mar. 2, 2005, 4 pages.

International Search Report issued in PCT/AU2003/001458, mailed Feb. 5, 2004, 5 pages.

International Preliminary Examination Report issued in PCT/AU2003/001458, completed Mar. 7, 2005, 7 pages.

International Search Report and Written Opinion issued in PCT/AU2004/001483, mailed Nov. 26, 2004, 5 pages.

International Search Report and Written Opinion issued in PCT/AU2004/001484, mailed Nov. 29, 2004, 5 pages.

International Search Report and Written Opinion issued in PCT/AU2004/01485, mailed Feb. 7, 2005, 6 pages.

International Search Report and Written Opinion issued in PCT/AU2004/001486, mailed Jan. 6, 2005, 7 pages.

International Search Report and Written Opinion issued in PCT/AU2004/01487, mailed Jan. 27, 2005, 12 pages.

International Search Report and Written Opinion issued in PCT/AU2004/01488, mailed Dec. 15, 2004, 6 pages.

Supplemental European Search Report issued in EP Application 00934813, mailed 10/19/2006, 2 pages.

Supplemental European Search Report issued in EP 01971489, completed Nov. 22, 2006, 4 pages.

Supplemental European Search Report issued in EP Appl. No. 02748447, Feb. 6, 2007, 6 pages.

Supplemental European Search Report issued in EP Appl. No. 04789624, mailed Mar. 6, 2008, 7 pages.

Supplemental European Search Report issued in EP 04789625, mailed Nov. 18, 2009, 6 pages.

Office Action issued in JP Application No. 2004-552261, dated Mar. 2, 2010.

\* cited by examiner

PERCUTANEOUS GAS-LINE

FIELD OF THE INVENTION

The present invention relates generally to a heart assist device, system and method and more particularly to a percutaneous gas-line for an implanted medical device such as a left ventricular assist device (LVAD), or counter-pulsation or co-pulsation heart assist device and to a heart assist device incorporating such a gas-line.

BACKGROUND OF THE INVENTION

International PCT patent application no. PCT/US00/22992 (WO 01/13974) discloses a gas-driven device heart assist device, that requires a percutaneous positioned gas-line.

U.S. Pat. No. 6,132,363 discloses a percutaneous access device (PAD) system, that allows both gas and electrical transmission, that utilises an intermediary connector piece that has the patient's own fibroblasts cultured onto the hub of the PAD. This has the proposed advantage of reducing infection. However, its disadvantages include its large size, inflexible nature, and that implantation is a two or three staged procedure. Specifically, implantation involves making a large skin biopsy, isolating the fibroblasts from the biopsy and growing the cells, then culturing them onto the device (which is a 10 day process). When the culturing process has been completed, the PAD can be implanted in the abdomen, and then the counterpulsation device implanted.

It is an object of the present invention to provide an improved percutaneous gas-line that, at least in preferred embodiments, requires no antecedent preparation and has a low risk profile for infection, but which allows remedial action to be taken in the event that gas-line infection occurs. It is well known that infection related to percutaneous lines in general is influenced by the diameter, flexibility and nature of the material. As such, a smaller, more flexible and soft (particularly Silicone) material are most advantageous in reducing infection—this is in direct contrast to the PAD as disclosed above.

It is a further object to provide a gas line for a heart assist device which gas line incorporates an ECG lead to provide for monitoring of the heart internally of the patient's body to control the operation of the heart assist device.

SUMMARY OF THE INVENTION

Accordingly, in a first aspect, the present invention provides a percutaneous gas-line for a medical device, the gas-line including:

a first gas-line part adapted to be wholly implanted in a patient and having a first end adapted for sealing connection to the medical device and a second end with a connection fitting; and a second gas-line part adapted to be part-implanted and part-external and having a first (external) end adapted for sealing connection to an external driver and a second (implanted) end adapted for removable sealing connection with the connection fitting on the second end of the first gas-line part.

The second gas-line part is preferably further adapted to be removable, for replacement, in the presence of persistent exit-site infection or damage to the external part.

The medical device is preferably a heart assist device, more preferably a left ventricular assist device (LVAD), or a counter-pulsation or co-pulsation heart assist device.

The first (external) end of the second gas line is preferably removably connected to the external driver.

In preferred embodiments of the invention, an ECG lead adapted to connect a patient's heart with a control system for a heart assist device utilising the gas line according to this invention is incorporated into the first gas line part and/or the second gas line part.

The second gas-line part is preferably constructed to have a minimal outside diameter, more preferably less than 7 mm, and has high flexibility and a resistance to kinking or collapsing. The second gas-line part is preferably made of a soft biocompatible, biostable material, such as silicone 45-65A durometer. This gas-line part may be wire-wound internally to allow thin wall and kink/collapse resistance.

The connection fitting is preferably a Luer-lock or similar gas-tight fitting.

The first and/or second gas-line parts preferably have a fluffy polyester, or similar, collar over about a short section (eg. 20-50 mm) of their implanted length. The collar being adapted to encourage sub-cuateous tissue ingrowth to help reduce any movement of the gas-line in situ—the collar is preferably at least 20 mm from the percutaneous exit site.

In a second aspect, the present invention provides a method of providing heart assistance to a patient using a percutaneous gas-line having a first gas-line part, adapted to be wholly implanted, and a second gas-line part, adapted to be part implanted and part external, connected to the first gas-line part, the method including the steps of:

(1) recognising a persistent exit-site infection;

(2) disconnecting the second gas-line part from the first gas-line part;

(3) removing the second gas-line part from the patient; and (4) connecting a sterile second gas-line part to the first gas-line part wherein the fresh second gas-line part is inserted through a fresh exit-site that is remote to the infected exit-site.

It will also be understood by persons skilled in the art that the fresh second gas-line part is inserted through an implant tunnel that is also substantially remote from the existing implant tunnel.

Alternatively, after step (3), the first gas-line part (and the implanted ECG cable, if it is attached to a corresponding interconnect cable associated with the second gas-line part) is sealed and wounds are closed to allow healing to occur (which may include prolonged treatment with antibiotics), at this time the device is non-functional, but can, at a later time, be made functional by re-implanting the second part and sealing attaching it to the first part.

In a third aspect, the present invention provides a gas line for connecting an inflatable heart assist actuator to a driver therefore, the gas line having a first end operatively connected to the inflatable actuator and a second end connectable, directly or indirectly through an extension gas line, to the driver for the heart assist actuator, the gas line having attached to it an ECG lead, the ECG lead having a first end adapted for connection to the heart of a patient and a second end adapted for connection to the driver or a controller for the driver, the attachment between the gas lead and the ECG lead being such that they are adapted to pass through the skin of a patient as a single element.

BRIEF DESCRIPTION OF THE DRAWINGS

A preferred embodiment of the invention will now be described, by way of an example only, with reference to the accompanying drawing in which.

DETAILED DESCRIPTION OF THE PREFERRED EMBODIMENT

Figure 1:
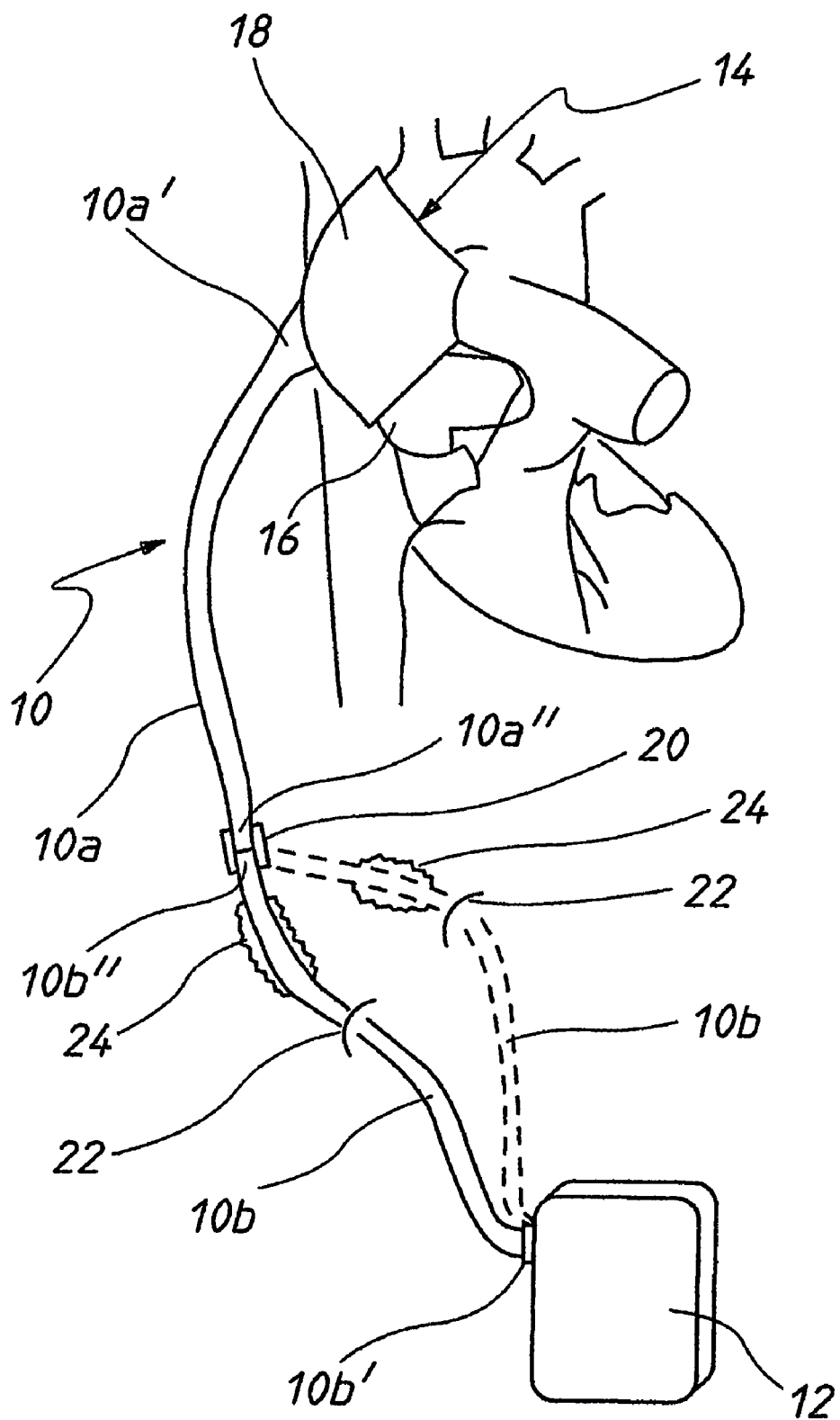
FIG. 1 is a schematic view of a percutaneous gas-line according to an embodiment of the invention, connected between an implanted heart assist device and an external driver.

FIG. 1 shows a percutaneous gas-line 10 according to a first embodiment of the invention. The gas-line 10 has a first part 10a and a second part 10b.

The gas-line 10 connects an external gas driver 12 to a left ventricle heart assist device 14, which is positioned around a patient's aorta 16. The heart assist device 14 comprises a balloon (not shown), a bushing (not shown), and a wrap 18 to hold the balloon in position around the aorta 16.

The first part 10a of the gas-line 10 has a first end 10a' sealingly connected to the bushing and in gas communication with the balloon. The first part 10a of the gas-line 10 also has a second end 10a" with a gas-tight Leur-lock fitting 20 thereon. The first part 10a of the gas-line 10 is made of a polyurethane-polysiloxane block co-polymer similar to that used to form the balloon and bushing.

The second part of 10b of the gas-line 10 is shown positioned percutaneous through an exit site 22. The external/un-implanted portion of the second part 10b has a first end 10b' that is connected to the external driver 12 with a gas tight but removable fitting. The second gas-line part 10b also has a second end 10b" connected to the second end 10a" of the first part 10a at the Luer fitting 20, such that the first gas-line part 10a and the second gas-line part 10b extend from the Luer fitting 20 in a substantially coaxial or straight configuration as shown. The implanted portion of the second part 10b also has about it a polyester collar 24 for anchoring the gas-line subcutaneously approx 20-50 mm from an exit site 22.

The second part 10b can be made of a different material to the first part 10a. It is preferably made of silicone or silicone-polyurethane co-polymer. The second part 10b can also be more flexible than the first part 10a and can be wire-wound.

In the event that the external part of the gas-line 10 is damaged in every-day use, or if a persistent infection develops at the exit site 22, then the second part 10b is able to be exchanged for a fresh/new (sterilised) second part 10b which is brought out of the patient via a new exit-site 22 (see phantom lines). As this can be done without need to replace the whole heart assist device arrangement, the surgery is minimal. More 25 particularly, the surgery only involves a small incision (not shown) over the subcutaneous connection, undoing of the connection of the Luer lock 20, and removal of the second part 10b. A new exit-site 22 is then made, and a new second part 10b tunnelled through to the first incision for reconnection of the first 10a and (new) second 10b parts. If the infection has travelled up the original second gas line part 10b then the fresh second gas-line part is 30 inserted through an implant tunnel that is also substantially remote from the existing implant tunnel.

Figure 2:
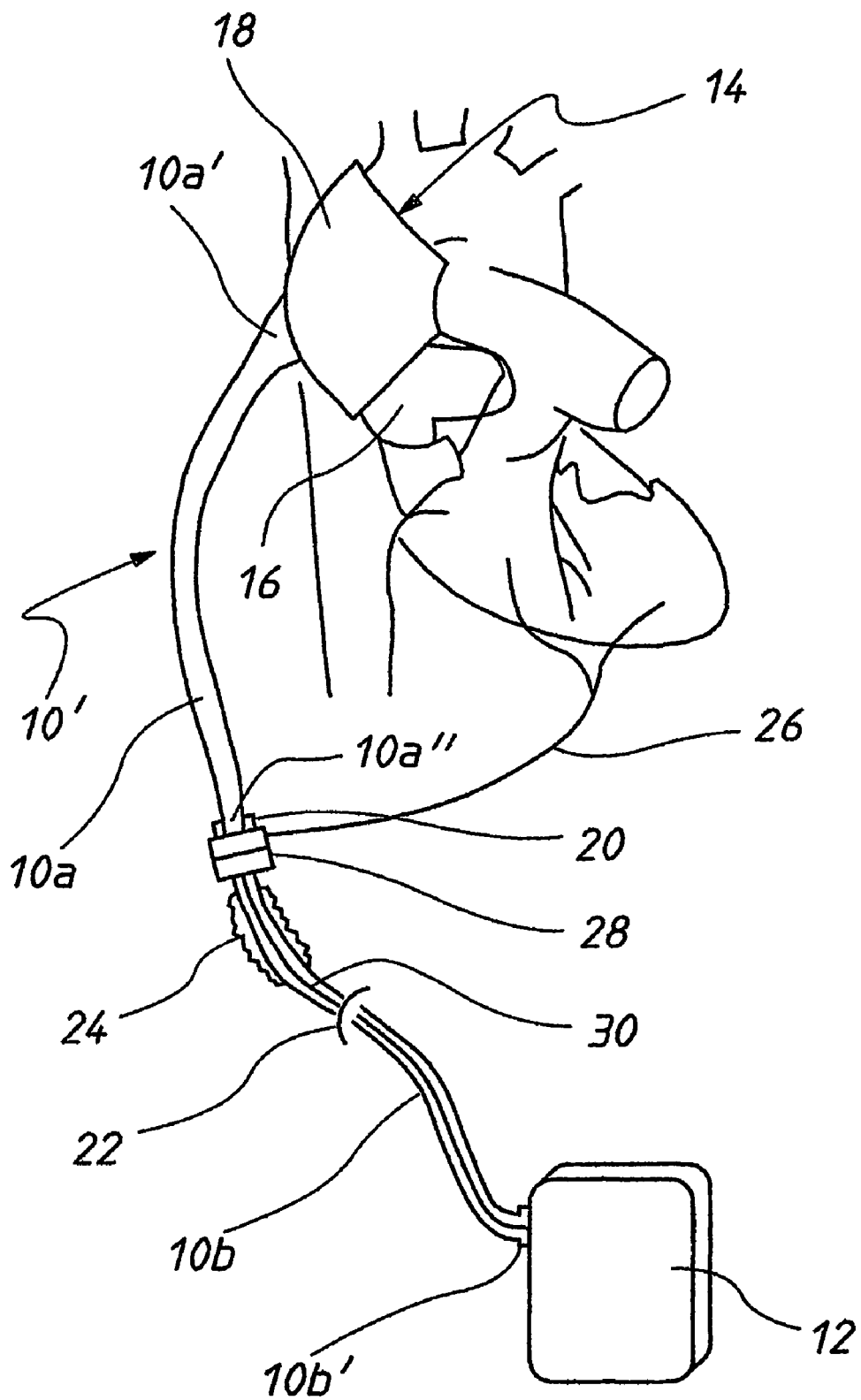
FIG. 2 is a schematic view of a percutaneous gas-line according to a second embodiment of the invention, connected between an implanted heart assist device and an external driver and in which an ECG cable is incorporated into the gas line.

FIG. 2 shows a percutaneous gas-line 10' according to a second embodiment of the invention. Like features to those of the first embodiment are indicated with like reference numerals in the second embodiment.

The gas-line 10' includes a first part (implanted) epicardial ECG lead 26, a sleeve 28 and a second part (percutaneous) ECG lead 30. The lead 26 enters the sleeve 28, which is connected between the first and second parts of the gas line 10a and 10b. The sleeve 28 has an electrical connector therein (not shown) that connects the lead 26 to an extension of the lead 30. The lead parts 26 and 30 therefore advantageously provide direct communication of ECG signals from the patient's heart to the driver 12.

The lead 30 is connected to the driver 12 and is contained within the interior of the gas-line second part 10b. Alternatively, the lead 30 can be glued to the exterior of the gas-line second part 10b. In either case, only a single exit site 22 is required, thereby minimising infection risk and patient discomfort.

It will be appreciated by the persons skilled in the art that numerous variations and/or modifications can be made to the invention as shown in the specific embodiment without departing from the spirit or scope of the invention as broadly defined. For example, the blood displacing devices are described above in relation to extra-aortic counter-pulsation but also suitable for intra aortic counter-pulsation devices, co-pulsation devices, or pneumatic driven LVADs.

The invention claimed is:

1. A percutaneous gas line for an implantable medical device, the gas line comprising:
   (a) a first gas line comprising a first end configured to be sealably coupled to the medical device and a second end;
   (b) a connection fitting configured to be disposed entirely within a patient's body, wherein the connection fitting is configured to be sealably coupled to the second end of the first gas line; and
   (c) a second gas line comprising:
      (i) a first end configured to be sealably and removably coupled to the connection fitting;
      (ii) a subcutaneous anchoring collar coupled around an outer surface of the second gas line along a length of the second gas line, wherein the collar is positioned in spaced relationship with the first end of the second gas line such that the collar is configured to be disposed within the patient's body when the first end is coupled to the connection fitting; and
      (iii) an opening defined in the first end, wherein the opening is in communication with a lumen defined within the second gas line, wherein the opening is substantially coaxial with a longitudinal axis of the gas line.

2. The percutaneous gas line of claim 1, further comprising an end portion defined between the first end of the second gas line and the subcutaneous anchoring collar, wherein the end portion extends from the connection fitting in a substantially coaxial configuration.

3. The percutaneous gas line of claim 1, wherein the second gas line comprises a second end configured to be sealably and removably coupled to an external driver.

4. The percutaneous gas line of claim 1, further comprising an ECG lead incorporated into the first gas line or the second gas line, wherein the ECG lead comprises a first end configured to be coupled to a control system and a second end configured to be positioned within the patient's body.

5. The percutaneous gas line of claim 1, wherein the subcutaneous anchoring collar comprises a fluffy polyester.

6. The percutaneous gas line of claim 1, wherein the subcutaneous anchoring collar has a length ranging from about 20 mm to about 50 mm.

7. The percutaneous gas line of claim 1, wherein the medical device comprises a heart assist device.

8. The percutaneous gas line of claim 7, wherein the heart assist device comprises a wrap configured to be disposed around an aorta of the patient.

9. The percutaneous gas line of claim 7, wherein the heart assist device is an inflatable heart assist actuator.

10. The percutaneous gas line of claim 1, wherein the medical device comprises a left ventricular assist device.

11. The percutaneous gas line of claim 1, wherein the connection fitting comprises a Luer-lock gas-tight fitting.

12. The percutaneous gas line of claim 1, further comprising an ECG lead associated with the second gas line.

13. The percutaneous gas line of claim 12, wherein the ECG lead is disposed within the second gas line.

14. The percutaneous gas line of claim 12, wherein the ECG lead is coupled to an exterior portion of the second gas line.

15. The percutaneous gas line of claim 12, wherein the ECG lead comprises a first part configured to be positioned within the patient's body and a second part associated with the second gas line.

* * * * *